(12) United States Patent
Kaspar

(10) Patent No.: US 8,530,436 B2
(45) Date of Patent: Sep. 10, 2013

(54) METHODS AND COMPOSITIONS FOR TRANSDERMAL DELIVERY OF NUCLEOTIDES

(75) Inventor: Roger Kaspar, Santa Cruz, CA (US)

(73) Assignee: Transderm, Inc., Salt Lake City, UT (US)

( * ) Notice: Subject to any disclaimer, the term of this patent is extended or adjusted under 35 U.S.C. 154(b) by 1637 days.

(21) Appl. No.: 11/699,772

(22) Filed: Jan. 29, 2007

(65) Prior Publication Data

US 2008/0181938 A1 Jul. 31, 2008

(51) Int. Cl.
*A61K 48/00* (2006.01)

(52) U.S. Cl.
USPC ......... 514/44; 536/24.5; 536/24.31; 536/24.1

(58) Field of Classification Search
None
See application file for complete search history.

(56) References Cited

U.S. PATENT DOCUMENTS

| | | |
|---|---|---|
| 5,993,851 A | 11/1999 | Foldvari |
| 6,720,001 B2 | 4/2004 | Chen et al. |
| 6,841,539 B1 | 1/2005 | Mehta et al. |
| 2002/0086356 A1 | 7/2002 | Tuschl et al. |
| 2003/0170630 A1 | 9/2003 | Alsobrook et al. |
| 2005/0026286 A1 | 2/2005 | Chi et al. |
| 2006/0015058 A1 | 1/2006 | Kellogg et al. |
| 2006/0069055 A1* | 3/2006 | Dajee et al. ............ 514/44 |
| 2006/0188531 A1 | 8/2006 | Jordan |

FOREIGN PATENT DOCUMENTS

| | | |
|---|---|---|
| JP | 2006-089475 | 4/2006 |
| WO | WO 94/17792 | 8/1994 |
| WO | WO 99/60167 | 11/1999 |
| WO | WO 0006120 A1 | 2/2000 |
| WO | WO 03/000174 | 1/2003 |
| WO | WO 2005059135 A2 | 6/2005 |
| WO | WO 2005/069736 | 8/2005 |
| WO | WO 2006/014035 | 2/2006 |
| WO | WO 2008/094866 | 8/2008 |

OTHER PUBLICATIONS

Marcel B. Bally et al., Biologial barriers to cellular delivery of lipid-based DNA carriers, Advanced Drug Delivery Reviews, 1999, pp. 291-315, 38.

R.M. Brand et al., Transdermal delivery of antisense compounds, Advanced Drug Delivery Reviews, 2000, pp. 51-57, 44.
Nagasawa M, et al., Inactivation of human viruses by providone-iodine in comparison with other antiseptics. Dermatology. 2002; 204 Suppl 1: 109-113.
Sickbert-Bennett EE et al., Comparative efficacy of hand hygiene agents in the reduction of bacteria and viruses. Am J Infect Control. Mar. 2005; 33(2): 67-77.
Scherer et al., Approaches for the Sequence-specific knockdown of mRNA, Nature Biotechnology, 2003, vol. 21, No. 12, Dec. 2003. p. 1457-1465.
Mahato et al., Modulation of gene expression by antisense and antigene oligodeoxynucleotides and small interfering RNA, Expert Opinion on Drug Delivery, Jan. 2005, vol. 2, No. 1, pp. 3-28.
Macron, Doug, RNAi Startup Believes siRNAs Can Treat Extremely Rare Skin Disorders (online).pp. 4-5, 2005, (retrieved on May 7, 2008), Retrieved from the Internet:URL:http://www.mainews.com.
Reynolds et al., Rational siRNA design for RNA interference. Nature Biotech vol. 22 No. 3 Mar. 2004 pp. 326-330.
Terrinoni et al., Novel and Recurrent Mutations in the Genes Encoding Keratins K6a, K16 and K17 in 13 Cases of Pachyonychia Congenita. Investigational Dermatology 117: pp. 1391-1396, 2001.
Smith et al., A Mutation in Human Keratin K6b produces a phenocopy of the K17 disorder pachyonychia congenita type 2. Human Molecular Genetics 7: pp. 1143-1148. 1998.
Lin et al., Identification of Sporadic Mutations in the helix initiation motif of keratin 6 in two pachyonychia congenita patients: further evidence for a mutational hot spot. Exp Dermatol 1998/1999 pp. 115-119.
Mahajan et al., Pachyonychia congenita-like nail changes treated successfully with a combination of vitamins A and E: A case report. Retrieved on Jun. 11 2008; vol. 69 Issue 5 pp. 338-339. http://www.ijdvl.com/article.asp?issn=0378-6323;year=2003;volume69;issue=5;spage=338;....
Soutschek et al., Therapeutic silencing of an endogenous gene by systemic administration of modified siRNA's. Nature 432; pp. 173-178. 2004.
IPPC 2004 meeting, Feb. 2004, (retrieved on May 8, 2008), Retrieved from the Internet : <URL:http://www.pachyonychia1.org/IPCC/IPCC.programs. AtaGlance-2004.pdf>.

\* cited by examiner

*Primary Examiner* — Kimberly Chong
(74) *Attorney, Agent, or Firm* — Thorpe North & Western LLP

(57) ABSTRACT

The present invention relates to formulations and related methods for transdermal delivery of nucleic acids. Specifically, the invention relates to a formulation containing lipids and an alcohol and which is capable of providing effective transdermal delivery of nucleic acid. The formulation can be used effectively to deliver nucleic acids for gene therapy and the treatment of disease.

13 Claims, 2 Drawing Sheets

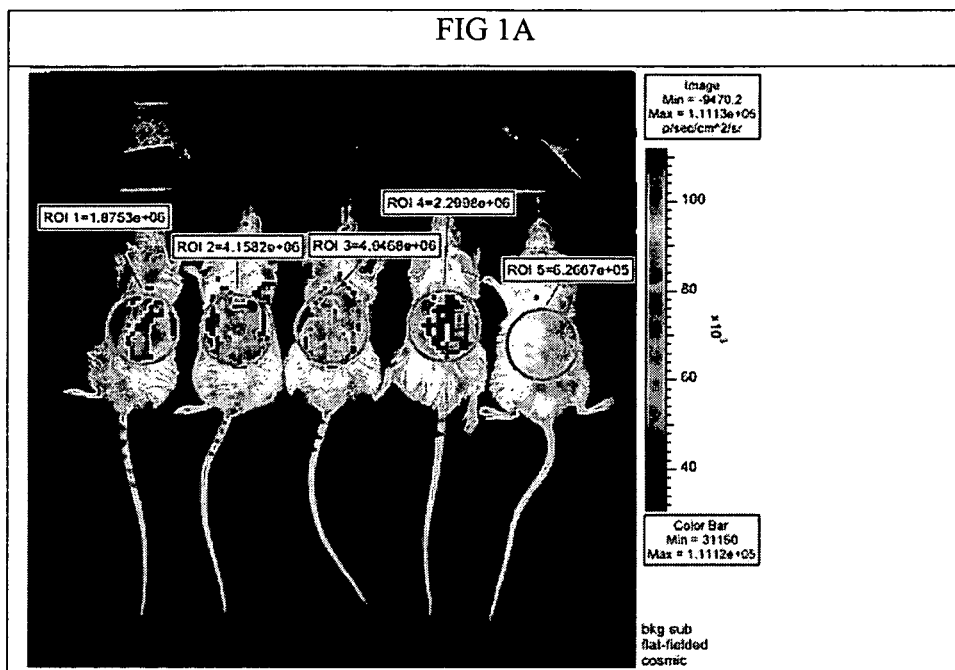
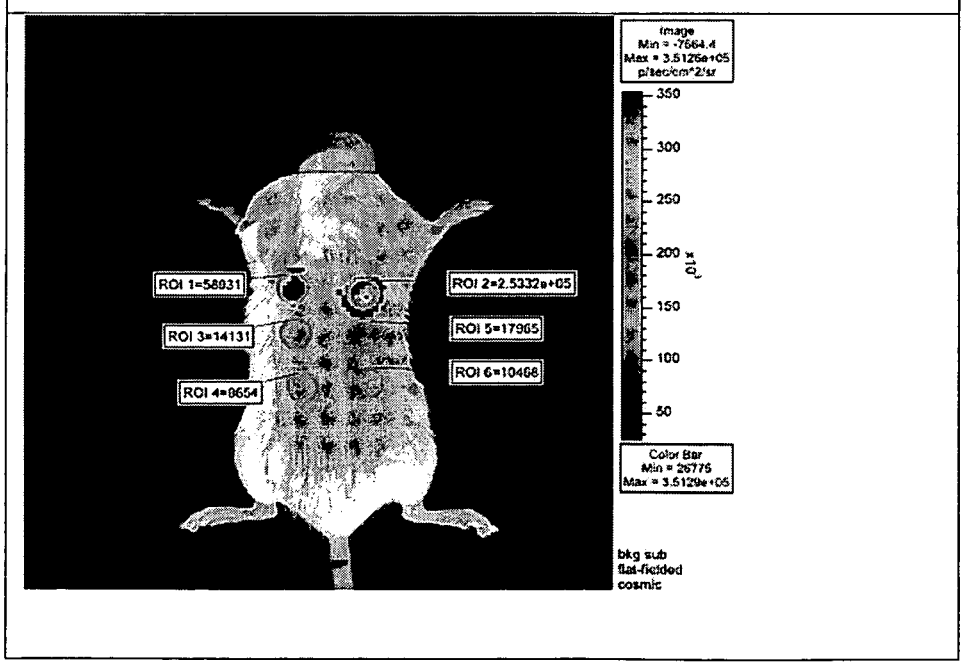

FIG. 2
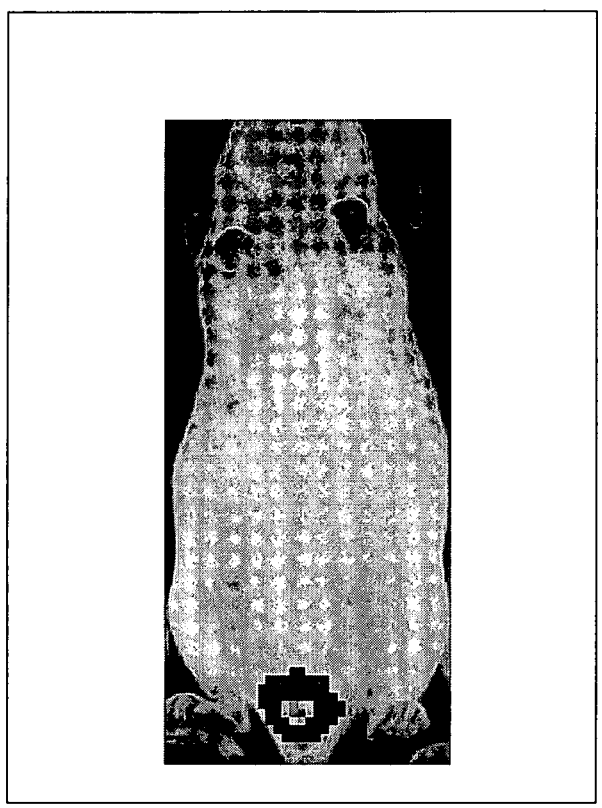
FIG. 3
FIG 3A
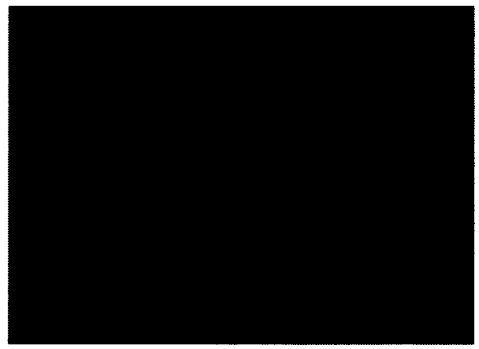
FIG 3B
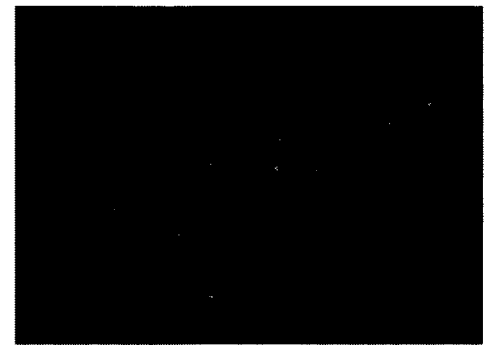

METHODS AND COMPOSITIONS FOR TRANSDERMAL DELIVERY OF NUCLEOTIDES

FIELD OF THE INVENTION

The present invention relates to formulations and methods for use in the transdermal delivery of oligonucleotides or polynucleotides. The formulations and methods can provide effective transdermal delivery of the oligonucleotides or polynucleotides in order to effectively treat a variety of conditions and disease.

BACKGROUND OF THE INVENTION

Control of genetic expression is envisioned as a potentially viable treatment for a variety of diseases or clinical conditions. There are two general approaches by which genetic expression is sought. One approach, gene therapy, aims to achieve such control of genetic expression by supplementing defective mutant allele with a functional one. Another approach, antisense therapy (including the use of siRNA), involves the synthesis and delivery of a strand of nucleic acid (DNA, RNA or a chemical analogue) that binds to the messenger RNA (mRNA) produced by a targeted gene and inactivates it, effectively inhibiting or "turning off" that gene. Regardless of the approach, one common hurdle to effective control over genetic expression exists, delivery of the nucleic acid to the target cells.

As such, research continues to find an effective means of delivery for nucleic acid to cells.

SUMMARY OF THE INVENTION

The present invention is drawn to a formulation for transdermal delivery of nucleic acids. In one embodiment, a composition for dermal delivery of nucleic acids is provided. The composition includes an amount of nucleic acids, at least one neutral lipid, and alcohol.

In another embodiment, a method for the transdermal delivery of nucleic acids includes applying an amount of a nucleic acid containing formulation to a skin surface. The nucleic acid containing formulation includes nucleic acids, at least one neutral lipid, and alcohol.

BRIEF DESCRIPTION OF THE DRAWINGS

FIG. 1—Shows in vivo mouse imaging of topically applied luciferase reporter gene after a 24-hour incubation period. Luciferase expression plasmid was topically applied to shaved mouse skin as part of a lipid/ethanol formulation. After a 24 hour incubation period, luciferin was injected IP and live mice were imaged by a high sensitivity, cooled LCD camera and quantified (red is highest luciferase expression). FIG. 1A shows four mice which received 25-50 μg of firefly luciferase plasmid. FIG. 1B shows a dose response of luciferase containing transdermal formulation (top left, middle left, middle right, bottom left were 75, 20, 5, and 0 μg total luciferase plasmid applied as part of the formulation); bottom right was a formulation containing 75 μg DsRed and acted as a negative control. The top right shows an intradermal injection control of 20 μg of luciferase plasmid dissolved in phosphate buffered saline.

FIG. 2—Shows in vivo mouse imaging of topically applied luciferase reporter gene to mouse cervix. Luciferase expression plasmid (20 μg of pCDNA 3.1fLuc) was topically applied to mouse cervix using a formulation of the present invention (see Example 3). After 24 hours, luciferin was injected IP and live mice were imaged by a high sensitivity, cooled LCD camera and quantified (red is highest luciferase expression).

FIG. 3—Shows tissue distribution of a transdermal formulation of the present invention. The formulation was topically applied to shaved mice. After 24 hours, the skin was frozen in OTC medium and microtome-sectioned. The formulation was visualized (due to fluorescent properties in the lipid component) by fluorescence microscopy FIG. 3A. The main regions of fluorescence are the hair follicles and the epidermis. A Brightfield image is shown in FIG. 3B.

DETAILED DESCRIPTION OF THE INVENTION

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting.

In describing and claiming the present invention, the following terminology will be used.

The singular forms "a," "an," and "the" include plural referents unless the context clearly dictates otherwise. Thus, for example, reference to "an RNA sequence" includes reference to one or more of such RNA sequences, and reference to "the genetic mutation" includes reference to one or more of such genetic mutation.

As used herein, "subject" refers to a mammal that may benefit from the administration of a nucleic acid containing composition or method of this invention. Examples of subjects include humans, and other animals such as horses, pigs, cattle, dogs, cats, rabbits, and aquatic mammals.

The term "gene" refers to a nucleic acid comprising an open reading frame encoding a polypeptide.

The term "nucleic acids" when used in connection with the formulation of the present invention refers to polymerized nucleic acids in the form of oligonucleotides or polynucleotides.

As used herein "oligonucleotide" or "polynucleotide" are used interchangeably and refer to polymers of deoxyribonucleotides, ribonucleotides, and modified forms thereof in the form of separate fragment or as a component of a larger construct, in a single strand or in double strand form. The polynucleotides which can be used with the formulations of the present invention includes sense and antisense oligonucleotides or polynucleotides of DNA or RNA as appropriate to the desired delivery goals of the formulations. The DNA or RNA molecules may be complementary DNA (cDNA), genomic DNA, synthesized DNA or a hybrid thereof or an RNA molecule such as mRNA, siRNA, shRNA, and the like.

Oligonucleotides or polynucleotides for use in the invention can be obtained using hybridization methods well known in the art. DNA and RNA sequences may also be synthesized using automated nucleic acid synthesis equipment well known in the art. Use of in vitro transcription can be used to prepare RNAs, including shRNAs, using methods well known in the art. Use of the well-known polymerase chain reaction (PCR) is particularly preferred for generating mixtures of polynucleotides. Genomic nucleic acids may be prepared by means well known in the art.

The oligonucleotides or polynucleotides of the invention may contain a modified internucleoside phosphate backbone to improve the bioavailability and hybridization properties of the oligonucleotide or polynucleotide. Such linkages can include but are not limited to phosphodiester, phosphoroanilotheiate, phosphoroanilidate, phosphoramidate, phosphorothiate, phosphorodithiate, or combinations thereof.

The oligonucleotide or polynucleotide may be part of a gene construct or an expression vector. The terms "gene construct" or "expression vector" refer to DNA or RNA molecules that comprise an oligonucleotide or polynucleotide which encodes a target protein and which includes initiation and termination signals operably linked to regulatory elements including a promoter and polyadenylation signal capable of directing expression in a target cell.

As used herein, the terms "target cell" or "target cells", refer to cells which receive the nucleic acids delivered using the transdermal formulations of the present invention.

As used herein, the term "inhibition of" or "silencing of" with respect to genetic expression refers to the absence of, or at least an observable decrease in, the level of protein from a target gene.

The term "expression" with respect to a gene sequence refers to transcription of the gene and, as appropriate, translation of the resulting mRNA transcript to a protein.

As used herein, "effective amount" or "therapeutically effective amount" of a nucleic acid refers to a sufficient amount of the nucleic acid to perform an intended task and achieve an intended result. For example, an effective amount of siRNA may be an amount which is sufficient to silence expression of a keratin gene. It is understood that various biological factors may affect the ability of a particular RNA sequence to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine.

As used herein, the terms "formulation" and "composition" are used interchangeably and refer to a mixture of two or more compounds, elements, or molecules. In some aspects the terms "formulation" and "composition" may be used to refer to a mixture of one or more nucleotide sequences with a carrier or other excipients.

The term "transdermal" refers to the route of administration that facilitates transfer of a drug through a skin surface wherein a transdermal formulation is administered to the skin surface.

The term "skin" or "skin surface" is meant to include not only the outer skin of a subject comprising one or more of epidermal layers, but also to include mucosal surfaces to which a drug composition may be administered. Examples of mucosal surfaces include the mucosa of the respiratory (including nasal and pulmonary), oral (mouth and buccal), vaginal, and rectal cavities. Hence the terms "transdermal" may encompass "transmucosal" as well.

The terms "enhancement", or "permeation enhancement," mean an increase in the permeability of the skin, to a drug, so as to increase the rate at which the drug permeates through the skin. Thus, "permeation enhancer" or simply "enhancer" refers to an agent, or mixture of agents that achieves such permeation enhancement.

"Topical formulation" means a composition in which the drug may be placed for direct application to a skin surface and from which an effective amount of the drug is released.

As used herein, the term "about" is used to provide flexibility to a numerical range endpoint by providing that a given value may be "a little above" or "a little below" the endpoint.

As used herein, sequences, compounds, formulations, delivery mechanisms, or other items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.5 to 10 g" should be interpreted to include not only the explicitly recited values of about 0.5 g to about 10.0 g, but also include individual values and sub-ranges within the indicated range. Thus, included in this numerical range are individual values such as 2, 5, and 7, and sub-ranges such as from 2 to 8, 4 to 6, etc. This same principle applies to ranges reciting only one numerical value. Furthermore, such an interpretation should apply regardless of the breadth of the range or the characteristics being described.

Unless otherwise defined, all technical and scientific terms used herein have the same meaning as commonly understood to one of ordinary skill in the art to which this invention belongs. Although any methods, devices and materials similar or equivalent to those described herein can be used in the practice or testing of the invention, representative methods, devices, and materials are described below.

The present invention relates to formulations and associated methods for effective transdermal delivery of oligonucleotides and/or polynucleotides. The formulations of the present invention can include lipids and ethanol. The formulations can also include an antimicrobial and/or a permeation enhancer.

The formulations of the present invention can be used effectively to deliver nucleic acids to the skin itself or to the underlying tissue depending on the nature disease or disorder being treated and the targeted cells. In one embodiment the formulations of the present invention can be used to treat disorders of the skin by delivering nucleic acids to target cells located in the skin. Examples of such disorders include but are not limited to pachyonychia congenita, keratosis pilaris, psoriasis, dermatitis, other hyperkeratin expression disorders, and the like. As would be understood by those in the art, the nature and sequence of the nucleic acid delivered by the formulation would vary depending on the disorder or disease being treated.

A variety of lipids can be used in the formulations of the present invention. In one embodiment the lipids are neutral lipids. Non-limiting examples of lipids which can be used include phosphatidylcholines such as 1,2-dioleoyl-snglycero-3-phosphoethanolamine, 1,2-diphytanoyl-sn-glycero-3-phosphoethanolamine, and 1,2-dimyristoyl-glycero-3-phosphoethanolamine, stearic acid, palmitic acids, and combinations thereof.

In one embodiment of the present invention, the lipids and alcohol are present in the formulation at a lipid to alcohol weight ratio of from about 1.5:1 to about 4.5:0.5 by weight. In another embodiment the lipid to alcohol weight ratio is from about 1.8:1 to about 3.5:1. In yet a further embodiment the lipid alcohol weight ratio is from about 2:1 to about 3:1. And in yet another embodiment the lipid alcohol weight ratio is from about 2.5:1 to about 3:1. Without being limited by theory, Applicants believe that the above lipid to alcohol ratios play a role in providing effective transdermal delivery of the nucleic acids in the formulation. The above described lipid to alcohol ratios also yield formulations which have appropriate and desirable consistencies for topical application.

Examples of alcohols which can be used in the formulations of the present invention include, but are not limited to, lower alcohols, ethanol, isopropyl alcohol, propanol, benzyl alcohol, methanol, other $C_4$-$C_{10}$ mono-alcohols, and mixtures thereof. In one embodiment the alcohol is ethanol.

The amount or concentration of nucleic acid which can be used in the present invention can vary. In one aspect, a concentration of nucleic acid in the formulation of about 50 µg/ml to about 2000 µg/ml (the volume refers to the volume of the formulation) may be used. In one embodiment the formulation can include from about 75 µg/ml to about 1500 µg/ml of nucleic acid. In yet another embodiment the formulation can include from about 100 µg/ml to about 1000 µg/ml nucleic acid. In a further embodiment the formulation can include from about 400 µg/ml to about 800 µg/ml nucleic acid.

The formulations of the present invention can also optionally include an antimicrobial compound. Generally, any antimicrobial compound can be used so long as it does not adversely affect the stability and durability of the formulations. In one embodiment, the antimicrobial compound is a quaternary ammonium salt, such as benzethonium chloride. For the purposes of the present invention, the term "quaternary ammonium salt" refers to a tetravalent nitrogen-containing molecule with a positive charge on nitrogen and a counter ion. Such quaternary ammonium salts include aliphatic and aromatic substituents. In addition to benzethonium chloride, other quaternary ammonium salts which may also be used include but are not limited to alkyl-, dimethyl benzenemethanaminium salt; acyl-, dimethyl benzenemethanaminium salt; mixed acyl-/alkyl-, dimethyl benzenemethanaminium salt; ethylbenzyl dodecyl dimethylammonium chloride, dodecylbenzyltrimethylammonium chloride, dodecylbenzyl triethanolammonium chloride, benzoxonium chloride; methylbenzethonium chloride; phenoctide; dodecarbonium chloride; and mixed alkyl-/acyl-, amidopropalkonium salt, or a mixture thereof. Other non-quaternary ammonium salt antimicrobial compounds may also be used.

In addition to their role as antimicrobials, in some aspects, the quarternary ammonium salts, especially, benzethonium chloride, can also act as permeation enhancers for the nucleic acids. Other permeation enhancers may also be used including but not limited to fatty acids, fatty acid esters, fatty alcohols, fatty acid esters of lactic acid or glycolic acid, glycerol triesters, glycerol diesters, glycerol monoesters, triacetin, short chain alcohols, urea, and mixtures thereof.

The formulations of the present invention can be applied as a cream or they can be formulated into various other delivery forms including but not limited to gels, pastes, ointments, and patches and sprays. One type of transdermal patch which can be used with the formulations of the present invention is a liquid reservoir system (LRS) type patch. When used in an LRS patch, the formulation of the invention can be formulated to for confinement in a reservoir having an impermeable backing and a skin contacting permeable membrane, or membrane adhesive laminate providing diffusional contact between the reservoir contents (i.e. the formulation) and the skin. For application, a peelable release liner is removed and the patch is attached to the skin surface. LRS patches are known in the art of transdermal drug delivery. Examples without limitation, of LRS transdermal patches are those described or referred to in U.S. Pat. Nos. 4,849,224, 4,983,395, which are incorporated by reference in their entirety.

Depending on the delivery form, the formulations of the present invention can also include other excipients including emollients, thickeners, surfactants, and the like. Generally, any excipient known in the art can be used so long as it does not impede the effectiveness of the formulation in delivering the nucleic acid. It is also essential that any excipient used not cause degradation of the nucleic acid. It is also recognized that some compounds can play multiple roles in a formulation (e.g. a compound may be a surfactant and a permeation enhancer, or a compound may be a emollient and a surfactant).

Examples of thickeners which can be used in the present invention include but are not limited to colloidal thickeners such as silica, magnesium aluminum silicate, and the like; naturally-occurring polymeric materials such as sodium alginate, xanthan gum, quince seed extract, tragacanth gum, starch and the like, semi-synthetic polymeric materials such as cellulose ethers (e.g. hydroxyethyl cellulose, methyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol, polyacrylic acid polymers, polyacrylamide polymers, polymethacrylic acid polymers, polyvinyl acetate polymers, polyvinyl chloride polymers, polyvinylidene chloride polymers. Also useful herein are hydrophilic gelling agents which such as the acrylic acid/ethyl acrylate copolymers and the carboxyvinyl polymers sold by the B.F. Goodrich Company under the trademark of Carbopol resins. These resins consist essentially of a colloidally water-soluble polyalkenyl polyether crosslinked polymer of acrylic acid crosslinked with 0.75% to 2.00% of a crosslinking agent such as polyallyl sucrose or polyally pentaerythritol. Examples include Carbopol 934, Carbopol 940, Carbopol 950, Carbopol 980, Carbopol 951 and Carbopol 981. Mixtures of any of the above thickeners and/or gelling agents may also be used.

Examples of emollients which can be used in the present invention include but are not limited to hydrocarbon oils and waxes; silicone oils; triglyceride esters; acetoglyceride esters; ethoxylated glyceride; alkyl esters; alkenyl esters; fatty acids; fatty alcohols; fatty alcohol ethers; etheresters; lanolin and derivatives; polyhydric alcohols (polyols) and polyether derivatives; polyhydric alcohol (polyol) esters; wax esters; beeswax derivatives; vegetable waxes; amides; and mixtures thereof Examples of surfactants which can be used in the present invention include but are not limited to polyethoxylated fatty acids such as PEG-fatty acid monoesters such as and esters of lauric acid, oleic acid, and stearic acid; fatty acid diesters such as PEG fatty acid diesters; alcohol-oil transesterification products such as PEG-35 castor oil (Incrocas-35), PEG-40 hydrogenated castor oil (Cremophor RH 40), PEG-25 trioleate (TAGAT[R] TO), PEG-60 corn glycerides (Crovol M70), PEG-60 almond oil (Crovol A70), PEG-40 palm kernel oil (Crovol PK70), PEG-50 castor oil (Emalex C-50), PEG-50 hydrogenated castor oil (Emalex HC-50), PEG-8 caprylic/capric glycerides (Labrasol), and PEG-6 caprylic/capric glycerides (Softigen 767), PEG-5 hydrogenated castor oil, PEG-7 hydrogenated castor oil, PEG-9 hydrogenated castor oil, PEG-6 corn oil (Labrafil[R] M 2125 CS), PEG-6 almond oil (Labrafil[R] M 1966 CS), PEG-6 apricot kernel oil (Labrafil[R] M 1944 CS), PEG-6 olive oil (Labrafil[R] M 1980 CS), PEG-6 peanut oil (Labrafil([R] M 1969 CS), PEG-6 hydrogenated palm kernel oil (Labrafil[R] M 2130 BS), PEG-6 palm kernel oil (Labrafil[R] M 2130 CS), PEG-6 triolein (Labrafil[R] M 2735 CS), PEG-8 corn oil (Labrafil[R] WL 2609 BS), PEG-20 corn glycerides (Crovol M40), and PEG-20 almond glycerides (Crovol A40); polyglycerized fatty acids such as polyglyceryl oleate (Plurol Oleique), polyglyceryl-2 dioleate (Nikkol DGDO), and polyglyceryl-10 trioleate. Preferred hydrophilic surfactants include polyglyceryl-10 laurate (Nikkol Decaglyn 1-L), polyglyceryl-10 oleate (Nikkol Decaglyn 1-O), and polyglyceryl-10 mono, dioleate (Caprol[R] PEG 860); propylene glycol fatty acid esters such as propylene glycol monolaurate (Lauroglycol FCC), propylene glycol ricinoleate (Propymuls), propylene glycol monooleate (Myverol P-06), propylene glycol dicaprylate/dicaprate (Captex[R] 200), and propylene glycol dioctanoate (Captex[R] 800); mono- and diglycerides such as glyceryl monooleate (Peceol), glyceryl 15 ricinoleate, glyceryl laurate, glyceryl dilaurate (Capmul[R] GDL), glyceryl dioleate (Capmul[R] GDO), glyceryl mono/dioleate (Capmul [R] GMO-K), glyceryl caprylate/caprate (Capmul[R] MCM), caprylic acid mono/diglycerides (Imwitor[R] 988), and mono- and diacetylated monoglycerides (Myvacet[R] 9-45); sterols and sterol derivatives; polyethylene glycol sorbitan fatty acid esters; polyethylene glycol alkyl ethers; sugar esters; polyethylene glycol alkyl phenols; polyoxyethylene-polyoxypropylene block copolymers; sorbitan fatty acid esters such as sorbitan monolaurate (Arlacel 20), sorbitan monopalmitate (Span-40), sorbitan monooleate (Span-80), sorbitan monostearate, and sorbitan tristearate; lower alcohol fatty acid esters; ionic surfactants such has sodium oleate, sodium lauryl sulfate, sodium lauryl sarcosinate, sodium dioctyl sulfosuccinate, sodium cholate, sodium taurocholate, lauroyl carnitine, palmitoyl carnitine, and myristoyl carnitine; unionized ionizable surfactants; ionizable surfactants; and mixtures thereof.

The formulations of the present invention are effective in transdermally delivering nucleic acids to the dermal tissue. The formulations may also be used effectively in combinations with other transdermal delivery means including but not limited to iontophoresis, needle arrays, sonication, occlusion, electroporation, and the like. Such technologies are well within the knowledge and capacity of one of ordinary skill in the art.

EXAMPLES

Example 1

Formulation for Transdermal Delivery of Nucleic Acids

A formulation for the transdermal delivery of nucleic acids is prepared in accordance with Table 1:

| Ingredient | Amount |
| --- | --- |
| Neutral Lipid Mixture | 2 grams |
| Ethanol | 0.875 ml |
| Aqueous Nucleic Acid Mixture | 2.5 ml |
| Benzethonium Chloride | 50 mg |

The formulation is prepared by vigorously stirring the ingredients of Table 1 at 50° C. to yield a homogenous stable cream. It is noted that the loading or concentration of nucleic acids in the nucleic acid mixture can vary in accordance with desired application. Loading values can be such that it the resultant formulation contains nucleic acid concentrations of from 50 μg/ml to about 2000 μg/ml.

Example 2

Formulation with Nucleic Acids

A formulation was prepared in accordance to Example 1 except that the nucleic acid mixture contained plasmid expression vector pCDNA 3.1fluc (Clontech) in an amount sufficient that the resulting formulation contained 500 mg/ml of nucleic acid. As in Example 1, the formulation was vigorously stirred at 50° C. and resulted in a stable cream. The prepared formulation was stored at 4° C.

Example 3

Transdermal Administration of Nucleic Acids to Mice

A nucleic acid formulation was prepared in accordance to Example 2. Approximately 100 μl of the formulation is applied to the backs of 6-8 week old shaved Balb/c mice. Following incubation periods of 12, 24, 48, and 96 hours, the mice were injected with luciferin IP (100 μl of 30 mg/ml luciferin; 150 mg/kg body weight). After 10 minutes the mice were anesthetized using isoflurane and were imaged using Xenogen IVIS in vivo imaging system. The results from the imaging are shown in FIG. 1A.

Example 4

Dosing Measures for Transdermal Nucleic Acid Formulations

Four nucleic acid formulations were prepared in accordance to Example 2 except that the amount of luciferase plasmid added to each (100 μl) was varied (Formulations 1-4: 75, 20, 5, and 0 μg luciferase). A fifth nucleic acid formulation was prepared in accordance with Example 2 except that the nucleic acid added was 75 μg of DsRed (Formulation 5). The DsRed was used as a negative control. Each of the Formulations 1-5 was topically applied to shaved mouse skin and, after 24 hours, each site was injected with luciferin. A sixth site was received an intradermal injection of 20 μg of the luciferase plasmid as well as the luciferin injection. After 10 minutes the mouse was anesthetized using isoflurane and was imaged using Xenogen IVIS in vivo imaging system. The results from the imaging are shown in FIG. 1B.

Example 5

Transdermal Administration of Nucleic Acids to a Mouse Cervix

A nucleic acid formulation was prepared in accordance to Example 2. An amount of the formulation containing approximately 20 μg of luciferase expression plasmid was topically applied to the cervix of a mouse. Following an incubation period of 24 hours, the mouse was injected with luciferin IP and then was subsequently imaged using a high sensitivity, cooled LCD camera. The luciferase expression was then quantitated (red being the highest luciferase expression). The result of the imaging is shown in FIG. 2.

Example 6

Tissue Distribution of the Nucleic Acid Transdermal Formulation

An amount of the formulation of Example 1 was applied topically to shaved mice. After a 24 hour period, the skin was frozen in OTC medium and microtome-sectioned. These skin sections were then visualized (using fluorescent properties in the lipid component of the formulation) by fluorescence microscopy FIG. 3A. A Brightfield image of the skin sections is shown in FIG. 3B. In FIG. 3A, the main regions of fluorescence are the hair follicles and the epidermis. These data indicate that the formulation readily penetrates the hair follicles as well as the epidermis.

Example 7

Nucleic Acid Transdermal Delivery Lotion Formulation

A nucleic acid formulation is prepared in accordance to Example 1, except that the formulation further includes an emollient. The formulation is particularly useful for the treatment of skin disorders or conditions. The nucleic acid provides direct treatment of the disorder while the emollient aids in treating the symptoms of the disorder.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A method of transdermally delivering nucleic acid to a subject, comprising:
applying an amount of a nucleic acid containing transdermal formulation to a skin surface of said subject, wherein said transdermal formulation comprises a mixture of neutral lipids and an alcohol and wherein the neutral lipids and the alcohol are present in the formulation at a ratio of neutral lipids to alcohol of from about 2.5:1 to about 3:1 by weight.

2. A method as in claim 1, wherein said transdermal formulation is in the form of a paste or cream.

3. A method as in claim 1, wherein said transdermal formulation is applied as a transdermal patch.

4. A method as in claim 1, wherein said skin surface is occluded following the application of the transdermal formulation.

5. A method as in claim 1, wherein the neutral lipids are selected from the group consisting of phosphatidylcholines such as 1,2-dioleoyl-snglycero-3-phosphoethanolamine, 1,2-diphytanoyl-sn-glycero-3-phosphoethanolamine, and 1,2-dimyristoyl-glycero-3-phosphoethanolamine, stearic acid, palmitic acids, and combinations thereof.

6. A method as in claim 1, wherein the nucleic acids are present in amounts of from 100 to 1000 µg/ml of the total composition.

7. A method as in claim 1, wherein the nucleic acids are present in amounts of from about 400 to 800 µg/ml of the total composition.

8. A method as in claim 1, wherein the composition further includes a biocide.

9. A method as in claim 8, wherein the biocide is benzethonium chloride.

10. A method as in claim 1, wherein the composition further includes a permeation enhancer.

11. A method as in claim 10, wherein the permeation enhancer is selected from the group consisting of a quaternary ammonium salt, fatty acids, fatty acid esters, fatty alcohols, fatty acid esters of lactic acid or glycolic acid, glycerol triesters, glycerol diesters, glycerol monoesters, triacetin, short chain alcohols, urea, and mixtures thereof.

12. A method as in claim 1, wherein the alcohol is selected from the group consisting of lower alcohols, ethanol, isopropyl alcohol, propanol, benzyl alcohol, methanol, other $C_4$-$C_{10}$ mono-alcohols, and mixtures thereof.

13. A method as in claim 12, wherein the alcohol is ethanol.

* * * * *